United States Patent [19]

Wild et al.

[11] Patent Number: 4,921,326

[45] Date of Patent: May 1, 1990

[54] FIBER OPTIC PROBE

[75] Inventors: Victor F. Wild, 5797 Honors Dr., San Diego, Calif. 92122; Michael Serrano, Lemon Grove; Eric J. Burtson, San Diego, both of Calif.

[73] Assignee: Victor F. Wild, San Diego, Calif.

[21] Appl. No.: 328,005

[22] Filed: Mar. 23, 1989

[51] Int. Cl.$^5$ .................... G02B 23/26; A61B 1/00
[52] U.S. Cl. ................... 350/96.26; 350/96.33; 350/96.25; 128/4; 128/6
[58] Field of Search ............... 350/96.25, 96.26, 96.32, 350/96.33; 128/4, 6; 362/32

[56] References Cited

U.S. PATENT DOCUMENTS

| | | | |
|---|---|---|---|
| 3,434,775 | 3/1969 | Gosselin | 350/96.26 |
| 3,494,354 | 2/1970 | Yokota et al. | 128/6 X |
| 3,773,039 | 11/1973 | Mori et al. | 128/6 X |
| 4,436,368 | 3/1984 | Keck | 350/96.33 |
| 4,730,096 | 3/1988 | Mizumoto | 350/96.25 X |
| 4,758,065 | 7/1988 | Dorman et al. | 350/96.25 |
| 4,768,858 | 9/1988 | Hussein | 350/96.33 X |
| 4,784,144 | 11/1988 | Ono et al. | 350/96.26 X |
| 4,826,280 | 5/1989 | Hiramoto et al. | 350/96.26 |
| 4,859,026 | 8/1989 | Arents | 350/96.25 |

FOREIGN PATENT DOCUMENTS 2584199  1/1987  France .................. 350/96.33

Primary Examiner—William L. Sikes
Assistant Examiner—Brian M. Healy
Attorney, Agent, or Firm—Kelly, Bauersfeld & Lowry

[57] ABSTRACT

A fiber optic probe is provided for use in viewing remote images, such as in vivo images in a biomedical environment or the like. The probe includes a tubular outer casing having an optical fiber of generally ring-shaped cross section, in combination with an inner fiber cable extending coaxially within the casing and defined by a coherent matrix or bundle of optical fibers. At a selected position spaced from a tip end of the probe, the inner cable passes through a gap in the fiber ring to the exterior of the casing for separate and relatively convenient coupling of the fiber ring and cable respectively to a light source and to image monitoring apparatus.

16 Claims, 2 Drawing Sheets

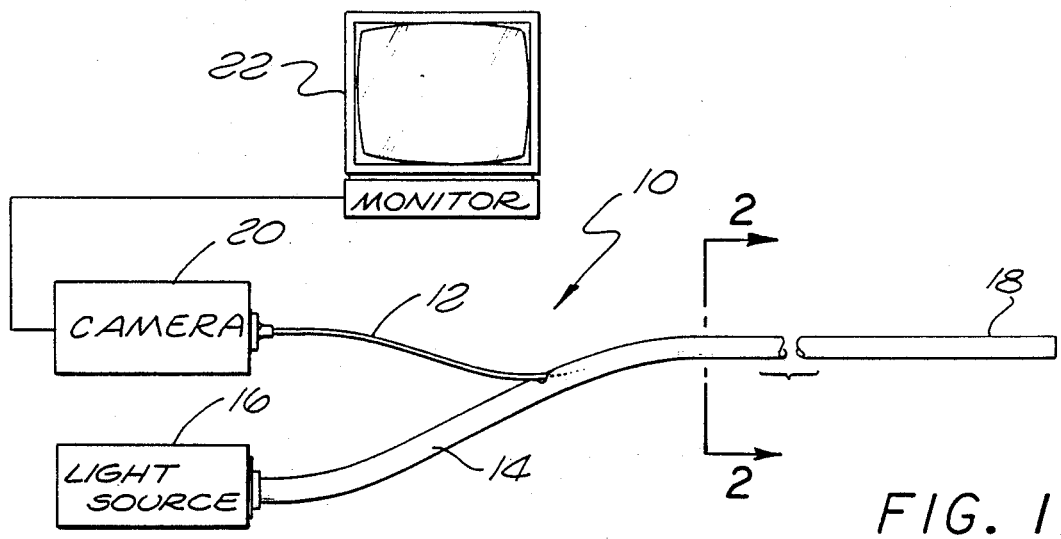
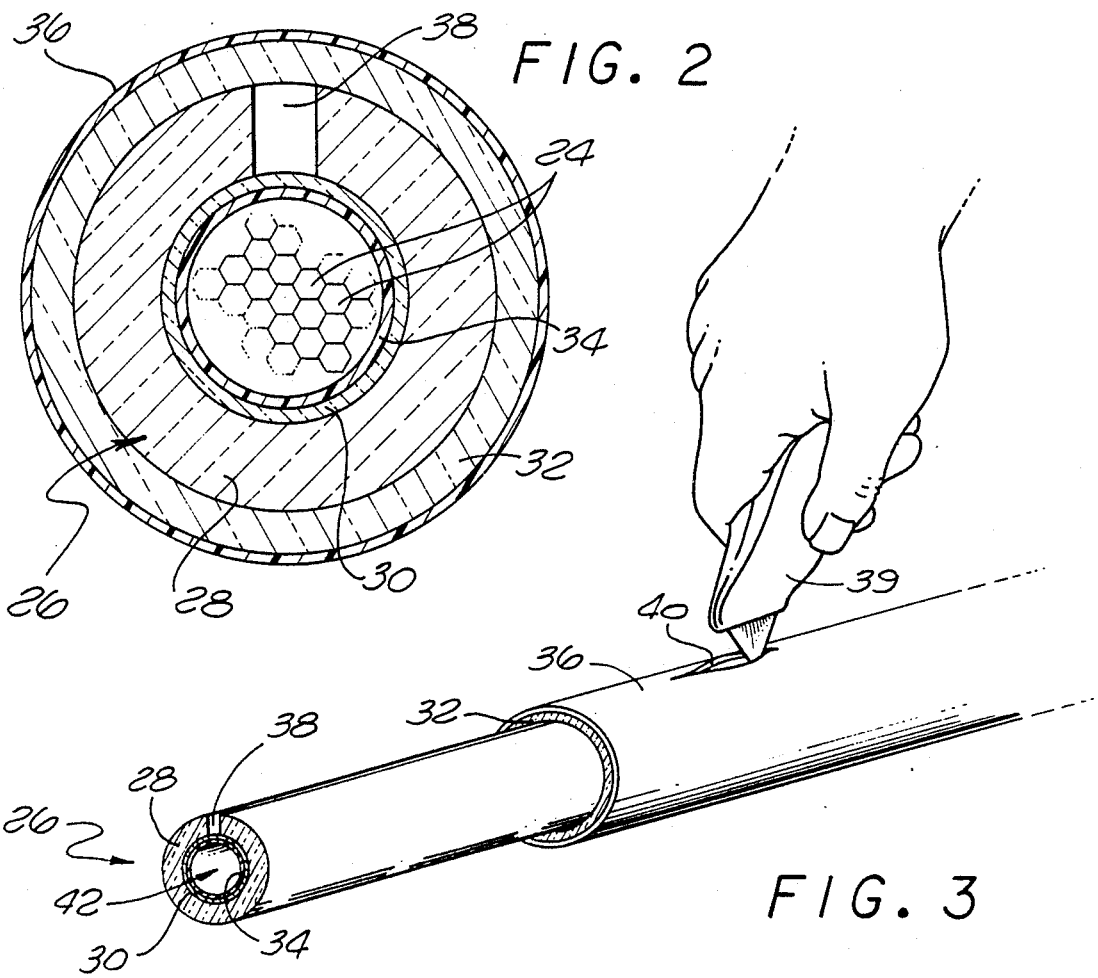

FIBER OPTIC PROBE

BACKGROUND OF THE INVENTION

This invention relates generally to improvements in fiber optic probes for use in viewing remote images in a biomedical environment or the like. More particularly, this invention relates to an improved fiber optic probe having a relatively simple and easily assembled construction, wherein the probe is adapted for facilitated separation of illuminating and reflected light.

Fiber optic probes are generally known in the art for use in viewing images located at remote or otherwise substantially inaccessible locations. For example, in recent years, fiber optic probes have been used in a variety of surgical and other biomedical applications to permit direct observation of internal issues and/or organs in the course of medical analysis and/or treatment. In such applications, a flexible fiber optic cable of relatively small diametric size and including multiple optical fibers is designed for tip end insertion into the body of a patient, typically by means of a catheter or the like. The fiber optic cable is manipulated to position the tip end at a selected in vivo location. A light source located externally of the patient transmits light through one or more of the optical fibers to illuminate the target in vivo subject, with additional optical fibers guiding light reflected from the target to an appropriate external camera or other monitoring apparatus for viewing.

In the past, fiber optic probes have been relatively complex in design and difficult to assemble in a cost efficient manner. More particularly, significant manual labor has been required to assemble the array of optical fibers into a compact cable geometry with separate groups of fibers providing adequate image illumination and sufficient coherent reflection to permit image viewing. Moreover, relatively complex optic devices have been required at the external end of the fiber cable for respectively coupling the fiber groups to an appropriate light source and to image monitoring equipment. As a result, fiber optic probes have been relatively costly and are generally incompatible for many biomedical applications and the like wherein probe disposal after a single use is desired.

There exists, therefore, a significant need for an improved fiber optic probe designed for volume manufacture and efficient assembly to provide an economical probe which can be disposed after a single use. The present invention fulfills these needs and provides further related advantages.

SUMMARY OF THE INVENTION

In accordance with the invention, an improved fiber optic probe is provided for viewing remote images, such as in a biomedical environment or the like. The probe comprises an outer fiber optic ring of generally annular cross section oriented coaxially about an inner fiber cable defined by a coherent matrix or bundle or optical fibers. The fiber optic ring transmits light to illuminate a selected image at a probe tip, with the image being viewed by monitoring light reflected back through the inner cable. At a selected point spaced from the probe tip, the inner cable passes through a gap in the fiber optic optic ring to the exterior, thereby separating the fiber optic ring and the inner cable in a generally Y-shaped geometry for separate and convenient coupling respectively to a light source and appropriate image monitoring equipment.

In accordance with the preferred form of the invention, the fiber optic ring is formed by extrusion or the like as part of a tubular outer casing. The fiber optic ring defines an elongated, generally cylindrical or tubular core which is suitably coated on the inner and outer surfaces thereof with cladding layers having an appropriate refractive index to insure light transmission through the core without significant attenuation. Protective inner and outer casing layers are applied in turn to the cladding layers, wherein the preferred casing layers comprise optically black coatings to isolate the fiber optic ring from the inner cable and surrounding environment.

The fiber optic ring is constructed with a longitudinally extending gap which extends for all or part of the length thereof. This gap defines an accessible exit site for passage of the inner fiber cable from a coaxial central bore of the casing tube to the exterior of the casing tube. In this regard, the inner fiber cable comprises a large plurality of small optical fibers arranged in a coherent matrix array and having a diametric cable size to permit relatively easy sliding reception into the central bore of the casing tube. The ends of the inner cable and the casing tube are generally aligned at the probe tip. From the tip, the inner cable extends through the casing tube to a selected point for exit passage to the exterior through the gap in thee fiber optic ring. The inner cable and the casing tube and thus separated in a generally Y-shaped configuration for easy coupling with monitoring equipment and a suitable light source.

In one form, the longitudinal gap in the outer fiber optic ring extends substantially the length of said ring to define a fluid flow path through the assembled prove. A selected fluid source may be appropriately coupled to this flow path, for example, at the point of exit passage of the inner cable from the casing tube, to selectively supply fluid through the probe flow path to the probe tip.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a schematic diagram representing a fiber optic probe constructed in accordance with the novel features of the invention;

FIG. 2 is an enlarged cross sectional view taken generally on the line 2—2 of FIG. 1;

FIG. 3 is a fragmented perspective view illustrating a casing tube for use in the fiber optic probe;

DETAILED DESCRIPTION OF THE PREFERRED EMBODIMENT

Figure 4:
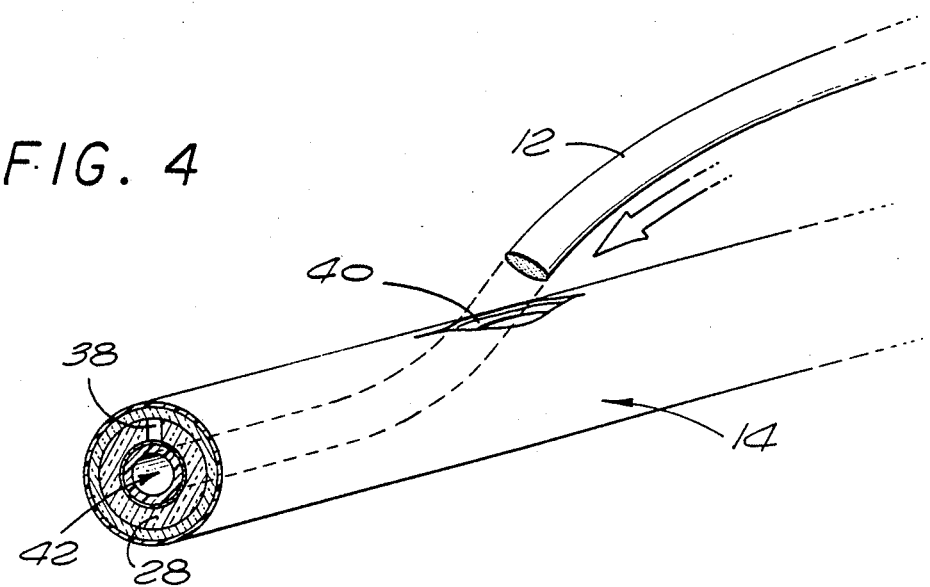
FIG. 4 is a fragmented perspective view illustrating insertion of fiber optic cable into the casing tube.

As shown in the exemplary drawings, an improved fiber optic probe referred to generally by the reference numeral 10 is provided for use in viewing remote images, such as in a biomedical environment or the like. The fiber optic probe 10 has a relatively simple, economical, and easily assembled construction to include a fiber optic cable 12 adapted for relatively easy insertion into an outer tubular casing 14. As viewed in FIG. 1, the casing 14 is adapted for coupling to suitable light source 16 and functions to guide light from the source 16 to a compact probe tip 18 to illuminate a target subject (not shown in FIG. 1). The inner fiber optic cable 12 transmits light reflected from the image back to a camera 20 or the like for image viewing on a monitor 22.

The improved fiber optic probe 10 of the present invention is particularly designed for use in biomedical applications wherein the probe tip 18 has a compact size and shape for transcutaneous insertion into the body of a patient. For example, as is known in the art, the probe tip 18 can be inserted into the body of a patient via a catheter or the like and then manipulated to place the probe tip at a selected in vivo position in close association with a target subject such as selected internal tissues and/or organs. The probe extends from the target subject to the exterior of the patient for coupling to the light source 16 and the camera 20 or other monitoring equipment to permit direct viewing of the target. Alternatively, it will be understood that the fiber optic probe 10 can be used in wide range of other image applications requiring the compact probe tip to illuminate and receive light reflected from a remote and/or other substantially inaccessible target. In accordance with the invention, the fiber optic probe 10 is designed for economical manufacture in a geometry which permits convenient and easy coupling to the associated light source and monitoring equipment, and wherein the probe can be discarded as a disposable item following a single use.

As shown in more detail in FIG. 2, the fiber optic probe 10 includes the inner fiber cable 12 consisting of a coherent matrix or bundle of large plurality of optical fibers 24. This plurality of optical fibers 24 is oriented in a predetermined or preorganized coherent array, as is known in the art, to permit transmission of individual segments of an image from one end of the cable to the other. While the specific size, design and number of fibers 24 utilized in the cable 12 may vary, small diameter cables having an outer diameter of about 0.02 inch and incorporating several hundred or more fibers 24 are known in the art.

The outer casing 14 of the probe 10 is shown generally in FIGS. 2 and 3 to have an elongated and hollow tubular construction which may be formed by extrusion processes or the like. The casing 14 includes an optical fiber ring 26 having a generally tubular core 28 with inner and outer cladding layers 30 and 32 of appropriate refractive index. The cladding layers 20 and 32 function in a conventional manner to confine light within the core 28 to substantially longituindal guided travel along the core without significant light loss. The cladding layers 30 and 32 are protected in turn by inner and outer casing layers 34 and 36 which are desirably opaque and preferably black in color. These casing layers 34 and 36 perform the dual functions of shielding the fiber ring 26 against physical damage while simultaneously isolating the fiber ring optically from the surrounding environment.

Figure 5:
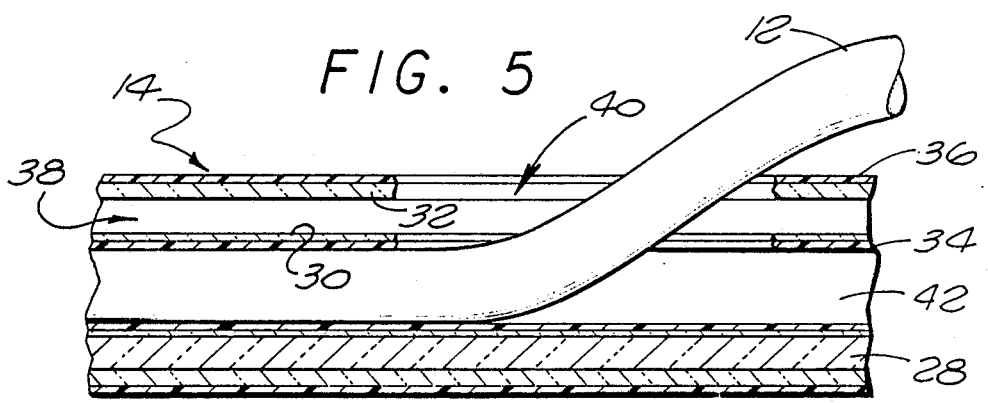
FIG. 5 is an enlarged fragmented longitudinal vertical section taken generally on the line 5—5 of FIG. 4.

In accordance with one primary aspect of the invention, the fiber optic ring 26 includes a gap 38 for passage of the inner fiber cable 12 therethrough. More particularly, in the preferred form of the invention, the fiber optic ring is constructed with a longitudinally extending, uninterrupted gap 38 extending throughout the length of the outer casing 14. This gap 38 can be exposed or accessed, as viewed in FIG. 2, at a selected point along the length of the casing by means of a knife 39 or the like to cut a short slit 40 in the outer protective casing layer 36 and the underlying outer cladding layer 32. By extending the slit 40 further through the inner cladding and protective layers 30 and 34, the multifiber inner cable 12 can be inserted through the slit 40 into a central bore 42 defined within the outer casing 14. Such insertion of the inner cable 12 is shown in FIGS. 4 and 5 which illustrate sliding feed insertion of the inner cable 12 into the casing 14. In this regard, the diametric size of the inner cable 12 is chosen to slide relatively freely yet with minimal clearance into the central bore 42 of the casing 14.

The inner cable cable 12 is fed into the outer casing 14 until a tip end of the inner cable is positioned generally at or in close proximity with a tip end of the casing 14. Such generally aligned tip ends of the cable and casing define the probe tip 18 of the fiber optic probe. In a preferred geometry, as viewed in FIG. 6, the tip end of the inner cable 12 is terminated in a slight inset position relative to the tip end of the casing 14 to permit insertion into the casing of a small focusing lens 44. As shown in the art, those tip ends of the casing and inner cable, as well as the focusing lens 44, are normally polished to maximize light transmission and resolution.

At the slit 40 in the casing 14, the inner cable 12 exits and separates from the casing 14 to provide a generally Y-shaped geometry. With this construction, the outer casing 14 can be coupled quickly and easily, and with relatively simple coupling devices, to the light source 16 (FIG. 1). Similarly, the inner cable 12 can be coupled quickly and easily with the camera 20. Costly devices for separating illuminating light from reflected light are not required due to the separation of the cable 12 and casing 14 at the slit 40.

Figure 6:
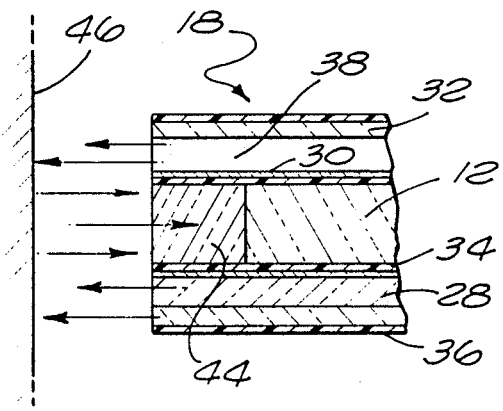
FIG. 6 is an enlarged fragmented longitudinal sectional view depicting a tip end of the fiber optic probe in association with a target image.

In use, the assembled fiber optic probe 10 is appropriately manipulated to position the probe tip 18 in close proximity with a target subject 46, as viewed in FIG. 6. In a biomedial environment, this positioning step normally involves insertion of the probe tip 18 to a selected in vivo site. At a convenient location along the probe 10, such as outside the body of a patient, the inner cable 12 exits the casing 14 through the slit 40 to permit separate connection to the light source 16 and the camera 20 (FIG. 1). The light source couples a light signal of appropriate intensity and duration for guided passage by the fiber optic ring 26 to illuminate the target subject 46. Light reflected from the target is guided by the inner cable 12 to the camera 20 for direct monitoring by means of the monitor 22.

The improved fiber optic probe 10 thus provides a simple and relatively cost efficient construction for use in viewing remote images. The probe 10 is designed for facilitated separation of illuminating and reflected light, and for simplified connection to a light source and monitoring equipment. Moreover, the simplicity of the probe design permits economical disposal after a single use.

Figure 7:
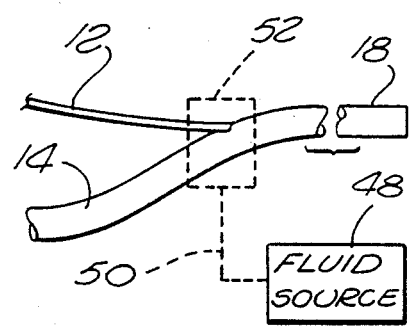
FIG. 7 is a schematic diagram similar to a portion of FIG. 1, but illustrating one alternative form of the invention.

In one alternative method of use, the longitudinal gap 38 in the outer fiber ring 26 may be used as a convenient fluid flow path leading to the probe tip 18. For example, as viewed in FIG. 7, a fluid source 48 may be provided for delivering a selected fluid through a conduit 50 and an appropriate coupling 52 for passage into the gap 38 in the fiber optic ring. With this arrangement, the fluid can be pumped to the probe tip. For example, a balloon catheter (not shown) mounted at the probe tip can be suitably inflated. Alternatively irrigation fluid can be delivered to the probe tip.

A variety of further modifications and improvements to the fiber optic probe 10 will be apparent to those skilled in the art. Accordingly, no limitation on the invention is intended by way of the foregoing description and accompanying drawings, except as set forth in the appended claims.

What is claimed is:

1. A fiber optic probe, comprising:
   a generally tubular casing having a fiber optic ring of generally annular cross section extending substantially the length thereof; and
   an inner fiber optic cable, said cable extending generally coaxially within said casing to a selected point along the length of said casing, said cable extending at said selected point through a gap formed in said fiber optic ring to the exterior of said casing, said gap extending longitudinally substantially the length of said ring.

2. The fiber optic probe of claim 1 wherein said inner fiber optic cable comprises a coherent matrix cable having a plurality of optical fibers.

3. The fiber optic probe of claim 1 wherein said casing further includes an outer protective layer encasing said fiber optic ring.

4. The fiber optic probe of claim 3 wherein said casing further includes an inner protective layer within said fiber optic ring.

5. The fiber optic probe of claim 4 wherein said inner protective layer is black.

6. The fiber optic of claim 4 wherein said inner and outer protective layers are opaque.

7. A fiber optic probe, comprising:
   a generally tubular hollow casing having a fiber optic ring carried therein and defining an elongated central bore, said fiber optic ring having a longitudinally extending and radially open gap formed therein; and
   an inner fiber optic cable defining a bundled plurality of optical fibers, said cable extending generally coaxially within said casing and having a first end generally aligned with a first end of said casing, said first ends of said cable and said casing defining a probe tip;
   said inner cable extending from said bore at a selected point along said casing through said gap in said fiber ring to the exterior of said casing, whereby said casing and said cable having a generally Y-shaped geometry at said selected point.

8. The fiber optic probe of claim 7 wherein said inner optical fiber cable comprises a coherent matrix cable having a plurality of optical fibers.

9. The fiber optic probe of claim 7 wherein said at least one optical fiber carried by said casing comprises a fiber optic ring of generally annular cross section and defining said bore.

10. The fiber optic probe of claim 7 wherein said casing further includes an outer protective layer encasing said fiber optic ring.

11. The fiber optic probe of claim 10 wherein said casing further includes an inner protective layer within said fiber optic ring.

12. The fiber optic probe of claim 11 wherein said inner protective layer is black.

13. The fiber optic probe of claim 11 wherein said inner and outer protective layers are opaque.

14. The fiber optic probe of claim 7 further including a light source connected to said casing and image monitoring means connected to said cable.

15. The fiber optic probe of claim 7 wherein said first end of said cable is inset slightly relative to said first end of said casing, and further including a focusing lens seated within said bore at said first end of said casing.

16. The fiber optic probe of claim 7 wherein said gap defines a fluid flow path.

* * * * *